United States Patent
Åkerfeldt et al.

(10) Patent No.: US 6,712,837 B2
(45) Date of Patent: Mar. 30, 2004

(54) GUIDING TOOL FOR WOUND CLOSURE ELEMENT

(75) Inventors: Dan Åkerfeldt, Uppsala (SE); Fredrik Preinitz, Uppsala (SE); Per Egnelöv, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 10/136,469

(22) Filed: May 2, 2002

(65) Prior Publication Data

US 2002/0173820 A1 Nov. 21, 2002

Related U.S. Application Data

(60) Provisional application No. 60/288,490, filed on May 4, 2001.

(30) Foreign Application Priority Data

May 3, 2001 (EP) ............................................. 01850081

(51) Int. Cl.[7] ................................................. A61B 17/00
(52) U.S. Cl. ....................................................... 606/213
(58) Field of Search .................................. 606/213, 214, 606/215, 212, 232, 151

(56) References Cited

U.S. PATENT DOCUMENTS

| 5,620,461 A | 4/1997 | Muijs Van De Moer et al. |
| 5,649,950 A | 7/1997 | Bourne et al. |
| 5,690,674 A * | 11/1997 | Diaz ........................ 606/213 |
| 5,725,519 A | 3/1998 | Penner et al. |
| 5,916,236 A | 6/1999 | Muijs Van de Moer et al. |
| 5,935,147 A | 8/1999 | Kensey et al. |
| 5,954,747 A * | 9/1999 | Clark ........................ 606/216 |
| 6,071,301 A * | 6/2000 | Cragg et al. ................ 606/213 |
| 6,086,607 A * | 7/2000 | Cragg et al. ................ 606/213 |
| 6,090,130 A * | 7/2000 | Nash et al. .................. 606/213 |
| 6,190,400 B1 * | 2/2001 | Van De Moer et al. .... 606/213 |

FOREIGN PATENT DOCUMENTS

WO    WO 01/13800    3/2001

OTHER PUBLICATIONS

U.S. patent application Ser. No. 09/704,726, Akerfeldt et al., filed Nov. 3, 2000.
U.S. patent application Publication No. 2001/0056254, Cragg et al., System and Method for Facilitating Hemostasis of Blood Vessel Punctures with Absorbable Sponge, Dec. 27, 2001.

* cited by examiner

*Primary Examiner*—Kevin T. Truong
(74) *Attorney, Agent, or Firm*—Foley & Lardner

(57) ABSTRACT

A guiding tool for controllable and reversible folding or deformation of a wound closure element before insertion into a percutaneous incision or puncture in the wall of e.g. a blood vessel, said incision or puncture being smaller than said wound closure element in an unfolded or undeformed state. It comprises a tubular member having a lumen. The lumen has inner walls provided with wound closure element guiding surfaces, adapted to reversibly reduce the spatial extension of a wound closure element during its passage through the guiding tool. A system for the introduction and securing of a wound closure element into a percutaneous incision or puncture in the wall of a vessel comprises such a guiding tool.

52 Claims, 3 Drawing Sheets

GUIDING TOOL FOR WOUND CLOSURE ELEMENT

This application claims The benefit of provisional application No. 60/288,490 filed on May 4, 2001.

The present invention relates generally to sealing of a percutaneous incision or puncture in the wall of a vessel, duct, lumen or hollow organ in the body of a living being, by positioning a sealing device in said incision or puncture, where the incision or puncture is smaller than said sealing device. In particular the invention relates to a guiding tool for enabling the correct positioning of such a sealing device, ensuring a leak-proof sealing.

BACKGROUND OF THE INVENTION

In recent years a number of devices and apparatuses have been developed enabling the closure or occlusion of e.g. punctures in the femoral artery following catheterization. Instead of applying a pressure to the puncture site for a period of time sufficient for blood clot formation to occur, the new methods are e.g. based on providing a plug, commonly referred to as an "artery plug", in the puncture. The plug is made of a resorbable material, such that it can be left in place until the tissue has recovered properly and the wound or puncture is healed. The plug can be made of collagen, and applied to the outside of a vessel against a counteracting element, also made of a resorbable material, introduced into the interior of the vessel. A locking means secures the collagen plug in place. A device of this kind is disclosed in U.S. Pat. No. 5,935,147 (Kensey et al). The sealing action is thus performed by the externally applied collagen plug. However, a certain percentage of applied plugs will not be leak-proof and often further compression by other devices or manually must be applied.

Alternatively, a plug can be made of two members such that a first member is positioned within a vessel and acts as the occluding member, and a second member is positioned outside the vessel and locked to the first member by a locking means. In order to ensure leak-proof action, the first member is larger than the puncture in all directions, i.e. it will cover a surface larger than the area of the puncture. In order to make this possible, the first member is foldable. A device of this kind is disclosed in our own EP-application EP-00850184.3 (corresponding to U.S. patent application Ser. No. 09/704,726).

The problem facing all systems wherein a folding or deformation of an element is needed in order to introduce the element into a vessel or through any tissue wherein the hole is smaller than the element itself, is that it can be difficult to achieve a reproducible unfolding, that accurately seals the hole from the inside. Also, in many cases the closure element is provided inside an introducer member such as a tube, in a folded state, already at the time of manufacture of the kit comprising all components. If the kit is stored for extended periods of time, and even for shorter times, the folded closure element most likely does not unfold properly at the time of use. To avoid the risk of permanent deformation, the closure element could be inserted into the introducer device by the physician, but this would require an extra manipulation, and it might be very difficult to maintain the sterility of the devices in such a case.

SUMMARY OF THE INVENTION

Thus, in view of the problem with the prior art devices, it is the object of the present invention to improve the rate of successful sealing operations using wound closure devices, when foldable or deformable closure elements are introduced into a vessel through a hole, smaller than the element itself, and to enable the folding and unfolding operation to take place during the sealing operation, and to avoid manipulation of the closure element by the physician at the time of performing the sealing operation.

This object is achieved by the provision of a guiding tool which in a controlled manner deforms or folds a wound closure element such that it after having been introduced through a puncture, unfolds and regains its original shape in a reproducible and controllable manner, and thereby provides adequate sealing at an excellent rate of success, this procedure taking place at the time of performing the sealing operation. The present invention relates to a guiding tool for controllable and reversible folding or deformation of a wound closure element before insertion of the wound closure element into a percutaneous incision or puncture in the wall of a vessel, duct, lumen, or hollow organ in the body of a living being, where the incision or puncture is smaller than the wound closure element in an unfolded or undeformed state. The guiding tool includes a body having a distal end, a proximal end, and a lumen extending between the distal and proximal ends. The guiding tool also includes a wound closure element introduction opening in the proximal end and a wound closure element exit opening in the distal end. The lumen has inner walls provided with wound closure element guiding surfaces. The wound closure element guiding surfaces are adapted to reversibly reduce the spatial extension of a wound closure element during its passage through the guiding tool so that the wound closure element is capable of passing through the incision or puncture and, after passing through the incision or puncture, assumes a shape that is capable of providing a sealing action against the incision or puncture.

DETAILED DESCRIPTION OF THE INVENTION

Figure 1A:
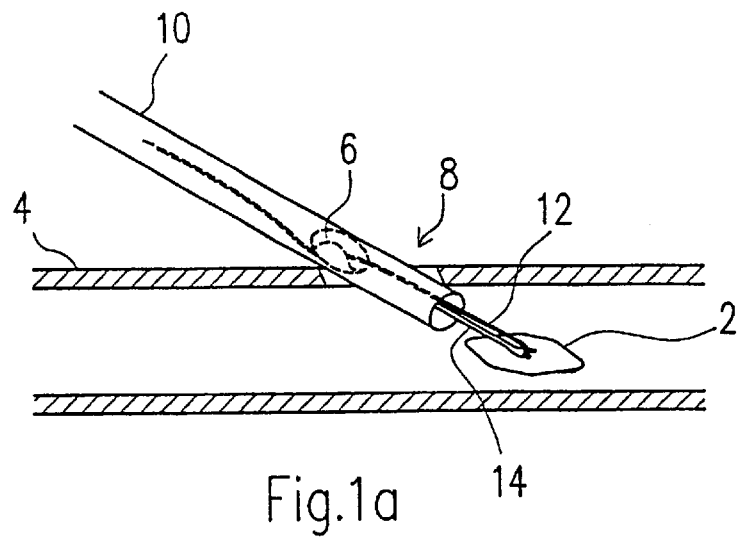
FIGS. 1a–c is a schematic illustration of a system for wound closure during operation thereof.
Figure 1B:
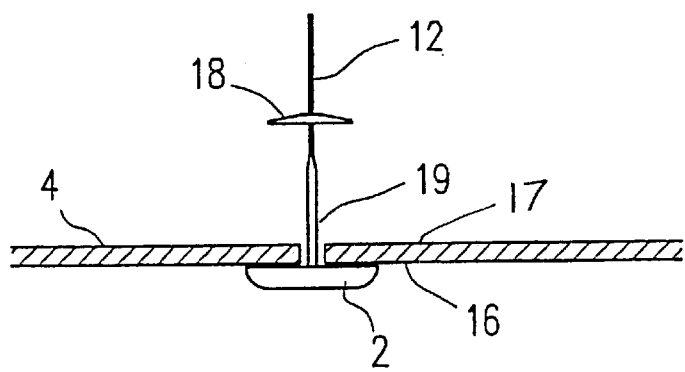
Figure 1C:
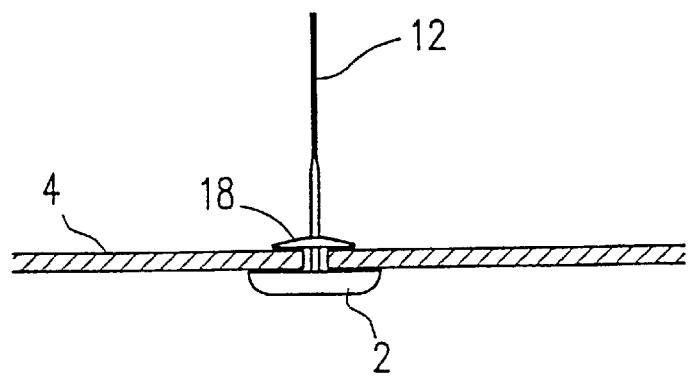

FIGS. 1a–c illustrates the procedure of inserting a wound closure (occlusion) element 2 in a blood vessel 4 and clamping it by means of a locking member 6. Thereby, an incision 8 is made in the blood vessel 4 in question, and an introducer tube 10 is inserted into the vessel 4, see FIG. 1a. Then, a folded, or in some other manner deformed closure element 2 is passed through said introducer tube 10 and into the vessel 4. The closure element 2 is secured to e.g. a suture 12, and some rigid elongated element 14 such as a steel pin or pusher rod (not shown) can be used to guide the closure element 2 through the tube 10 and into the vessel 4, where it unfolds. Once the closure element 2 has unfolded inside the vessel 4, the pusher rod and the introducer tube 10 are withdrawn from the vessel but maintained close to the exterior of the vessel 4. Then, the closure element 2 is pulled back using the suture 12, so as to be located in a position where it is held against the interior vessel wall 16, FIG. 1b. An essentially disk shaped locking element 18, having a central hole, is provided on the suture 12, the suture running through said hole, such that the locking member can be moved along the suture 12 to be brought into contact with the exterior vessel wall 17. By the provision of suitable friction enhancing means 19 on the very distal end of the suture, the locking element can be pushed against the wall of the vessel while engaging the portion of the suture having higher friction, and thereby cause a locking of the closure element, FIG. 1c. This principle is used in e.g. U.S. Pat. No. 5,916,236.

It is important that the closure element unfolds in a reproducible way, such that it will contact the inner vessel wall around the circumference of the incision. If the closure element is delivered to the user in a folded state, in position inside the introducer, as a "kit" ready for use by a physician, and the kit has been stored on a shelf for some time, it may happen that the closure element has become permanently deformed, and will not assume the desired shape (which may be to regain its original shape) inside the vessel. Such an event would of course dramatically increase the risk that the closure element will not fulfill its function, and cause a leakage.

Therefore, in accordance with the present invention, there is provided a guiding tool that is connectable to an introducer of the type discussed above, the closure element being provided in said guiding tool in an unfolded state. Thereby the actual deformation or folding of the closure element, necessary to enable insertion through the incision (which is smaller than the closure element) and into the blood vessel, is not performed until the time of performing the operation of inserting the closure element. In this way, the closure element will not be subjected to a prolonged deformation during storage.

Figure 2A:
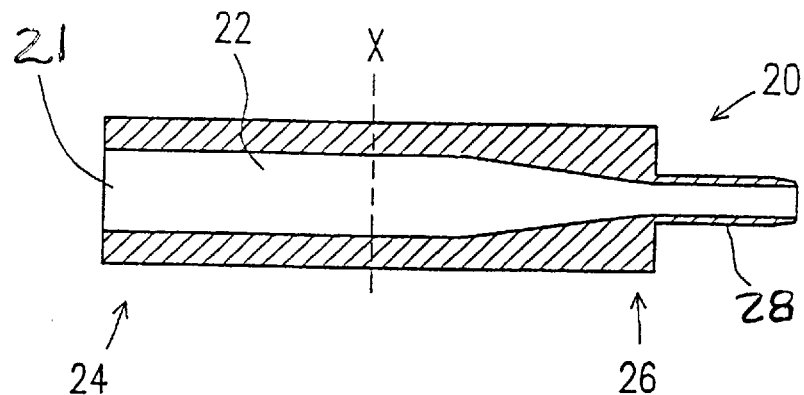
FIG. 2a illustrates a first embodiment of the guiding tool of the invention in cross section.

A first embodiment of the invention is illustrated in FIG. 2a. It comprises a body in the shown embodiment in the form of an elongated tube like member 20 (although cylindrical outer symmetry is no requirement), having an inner lumen 22 that has a first diameter in the proximal end portion 24 and over a fraction of its length (up to the dotted line X), forming a space 21 in which a closure element (not shown) can be housed without being deformed. Over a second fraction of the length, from the dotted line X and up to the distal end 26 portion, the lumen becomes narrower, rendering the lumen 22 cone shaped over this portion. Finally there is a connection portion 28, connectable to an introducer tube (such as the tube 10 in FIG. 1a). The exit diameter is equal to or slightly smaller than the inner diameter of the introducer tube, i.e. small enough to enable passing the closure element into the blood vessel.

Figure 2B:
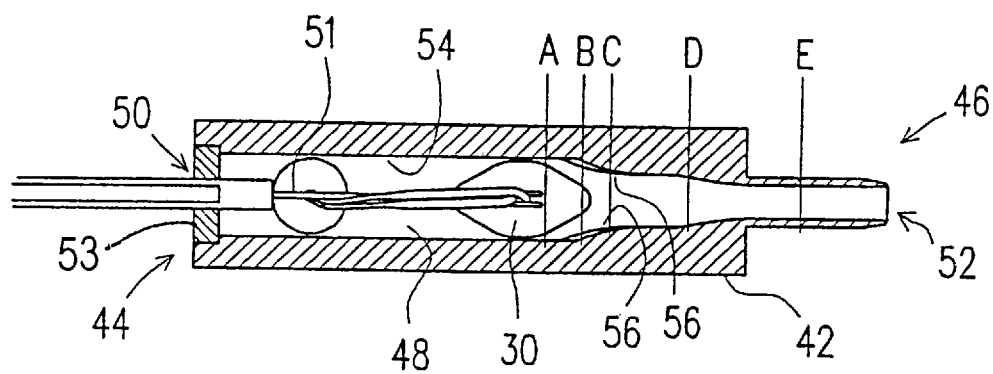
FIG. 2b is a view in longitudinal cross section of a second embodiment of the inventive guiding tool.
Figure 3A:
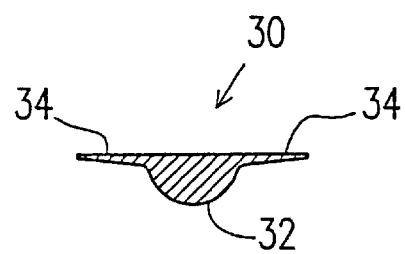
FIG. 3a is a cross section view of a closure element.
Figure 3B:
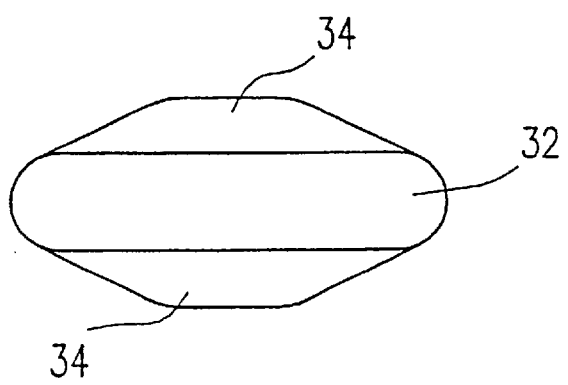
FIG. 3b is a top view of a closure element.

In FIG. 2b a second embodiment of the guiding tool according to the present invention is illustrated. It is adapted for a closure element 30 having the general shape shown in FIGS. 3a and 3b. The closure element suitable for use with the illustrated embodiment of the guiding tool, has a thick mid portion 32, that is generally elongated, and has peripheral wings 34 or edges, which are substantially thinner, and thus more flexible than the mid portion 32. The peripheral shape is like a slightly distorted ellipse, but could in principle be circular, the wings 34 thereby forming rather a collar or a brim surrounding the mid portion. Other shapes are also possible. A suitable kind of closure element is disclosed and claimed in our copending EP-00850184.3. In view of its flexibility, the wings 34 or rim are foldable such that the entire element will have a smallest dimension in a folded state that fits well within an incision or puncture in a blood vessel, thereby enabling insertion into said vessel.

Thus, the embodiment of the guiding tool according to the present invention shown in FIG. 2b, comprises an essentially tubular element 42 having a proximal end 44 and a distal end 46 and a lumen 48 extending between said distal 46 end and said proximal end 44. There is further a wound closure element introduction opening 50 in the proximal end 44, and a wound closure element exit opening 52 in the distal end 46. The distal end is shaped so as to be connectable to an introducer tube, like the one described above in connection with FIG. 1. The introduction opening 50 may optionally be provided with a sealing plug 53.

The lumen 48 has inner walls 54 provided with wound closure element deformation surfaces 56, adapted to deform a wound closure element during passage thereof, past said surfaces 56, through the guiding tool, from an essentially undeformed or unfolded state to a deformed or folded state. The effect of this deformation/folding should be such that the overall dimension of the wound closure element is changed to render it capable of passing through the puncture in the blood vessel. Also, after passage through said incision or puncture it must regain a shape that is capable of providing a sealing action against the inner wall of the vessel.

In FIG. 2b there is also shown a pusher rod 51, having a fork like configuration, that is used to push the closure element 30 through the introducer and into the blood vessel. This pusher rod is retracted once the element is properly located inside the vessel.

Figure 2C:
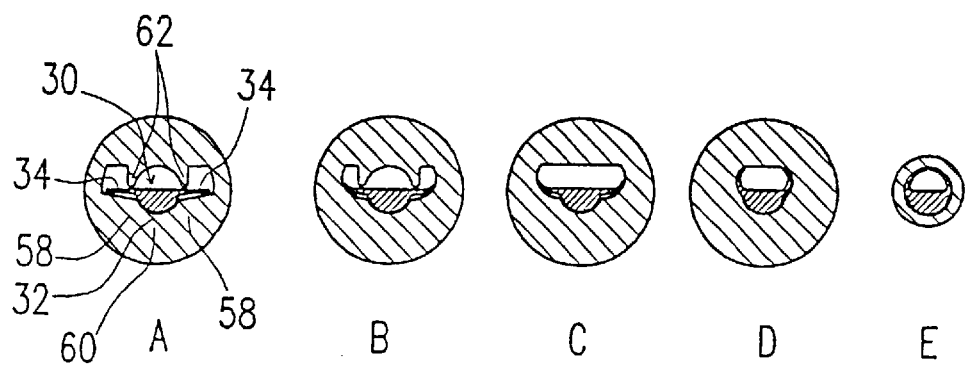
FIG. 2c illustrates cross sections at A-E in FIG. 2b.

In the embodiment shown in FIG. 2b the deformation surfaces 56 have a specific design, illustrated by a sequence in FIG. 2c, which are cross section views through the lumen at the positions indicated with corresponding letters A, B, C, D, E in FIG. 2b. Thus, there is one guiding surface 58 for each wing on the closure element 30, and a guiding recess 60 in which the thicker mid portion 32 of the closure element 30 will run during its passage through the guiding tool. The guiding surfaces will initially have an orientation such that the wings 34 of the unfolded or undeformed closure element 30, when inserted into the guiding tool in the introduction opening, will rest thereon in a position and orientation causing no deformation (referred to as a "horizontal" orientation; position A in FIG. 2c). Thereby the nominal shape of the closure element 30 is preserved also during extended storage. In a direction towards the exit opening, the guiding surfaces will gradually become elevated (A-B-C-D-E in FIG. 2c) from the initial, essentially horizontal orientation, and also curved such that they form what could be referred to as a "quasi-conical" lumen inside the tool. At the end of the lumen, near the exit opening, the guiding surfaces will have reached a state where the cross section of the lumen is essentially circular, and where the diameter corresponds to the inner diameter of the introducer tube.

Preferably, there are guiding rails 62 provided above the guiding surfaces 58, such that the wings or rims 34 of the closure element 30 will be kept down during the process of pushing it with the pusher rod through the guiding tool, thereby preventing inadvertent tilting or incorrect behavior of the closure element during the movement through said guiding tool. The rails are preferably integrated in the "roof" of the lumen. However, they can also be provided as an insert and attached by suitable means inside the lumen.

In a further variation of the above described embodiment, the interior lumen of the guiding tool essentially has a cross section that exactly corresponds to the cross section of the closure element. This lumen would then form a guiding slot inside the tool, whereby the slot would be shaped so as to gradually change from a cross section corresponding to the above mentioned "horizontal orientation" to an essentially circular cross section, the diameter of which would be smaller than the incision through which the closure element is to be inserted. There must however be a space above the closure element for the access by the pushing rod needed for advancing the closure element through the tool and the introducer.

The sequence A-E in FIG. 2c illustrates the folding process, and it is clearly seen that the closure element reaches a folded state where it conforms to the circular cross section of the introducer tube, which is connected to the guiding tool at the exit end thereof.

Figure 2D:
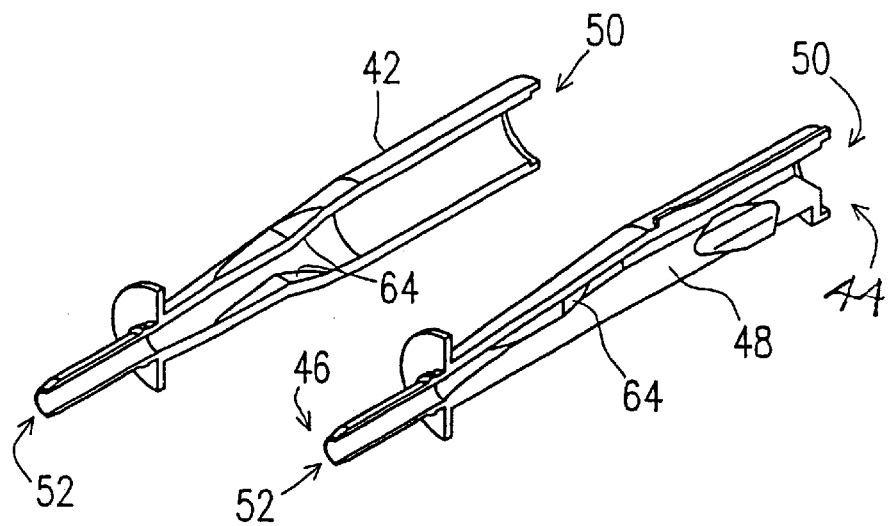
FIG. 2d is a perspective cut view in two different directions of a third preferred embodiment of the inventive guiding tool.

Another embodiment of the guiding tool is shown in FIG. 2d, showing perspective cuts through the device at two orientations perpendicular to each other. Like reference numerals are used for like elements in FIGS. 2c and 2d. Like in the above described embodiment, this embodiment of the guiding tool comprises an essentially tubular element 42 having a proximal end 44 and a distal end 46 and a lumen 48 extending between said distal 46 end and said proximal end 44. There is further a wound closure element introduction opening 50 in the proximal end 44, and a wound closure element exit opening 52 in the distal end 46. The distal end is shaped so as to be connectable to an introducer tube.

Also in this embodiment, the lumen 48 has inner walls 54 also provided with wound closure element deformation surfaces 56, adapted to deform a wound closure element during passage thereof, past said surfaces 56, through the guiding tool, from an essentially undeformed state to a deformed state.

However, the deformation surfaces have a different design in this embodiment. Namely, one wall of the inner lumen is flat such that the closure element can be placed essentially flat thereon, in an unfolded state, e.g. during shelf storage, corresponding to the "horizontal orientation" discussed above in connection with FIG. 2b, but with the thicker mid portion facing upwards. Towards the exit opening the lumen is shaped as cone, much like in the first embodiment of FIG. 2a, whereby the final diameter of the inner lumen corresponds to a diameter smaller than the diameter of the opening in the blood vessel through which the closure element is to be introduced. About half-way along the conical portion of the lumen, there are provided a pair of deflection surfaces 64, having a "steeper" angle than the over-all cone angle of the lumen. These surfaces will engage the peripheral rim or collar portions of the closure element, such that they are deflected or bent downwards from the essentially flat initial position. Also, the pusher rod discussed above will cause the closure element not to lie completely flat, but slightly angled with the trailing edge at a slightly elevated position compared to the leading edge. Furthermore, said pusher rod will assist in keeping the leading edge forced against the flat surface.

In order to facilitate correct positioning of the closure element during insertion, also in this case there may be provided guiding rails like those described above.

The invention having been described with reference to preferred embodiments thereof can be subject to alterations and modifications by the man skilled in the art, and the scope of the invention is limited only by the appended claims.

What is claimed is:

1. A guiding tool for controllable and reversible folding or deformation of a wound closure element before insertion of said wound closure element into a percutaneous incision or puncture in a wall of a vessel, duct, lumen or hollow organ in a body of a living being, said incision or puncture being smaller than said wound closure element in an unfolded or undeformed state, said guiding tool comprising:

a body having a distal end and a proximal end and a lumen extending between said distal end and said proximal end; and a wound closure element introduction opening in the proximal end, and a wound closure element exit opening in the distal end;

said lumen having inner walls provided with wound closure element guiding surfaces adapted to progressively fold a peripheral portion of a wound closure element in a direction toward a non-peripheral portion to reversibly reduce the spatial extension of the wound closure element during passage of the wound closure element through the guiding tool.

2. The tool as claimed in claim 1, wherein said introduction opening is larger than said exit opening.

3. The tool as claimed in claim 1, wherein said exit opening is smaller than said incision or puncture.

4. The tool as claimed in claim 1, wherein said guiding surfaces form an essentially conical inner lumen.

5. The tool as claimed in claim 1, wherein said guiding surfaces are separate deflection elements protruding from the inner wall of said lumen.

6. The tool as claimed in claim 1, wherein said guiding surfaces in the proximal end of said tool are essentially flat, and in a direction towards the distal end, gradually become elevated and also curved such that the guiding surfaces form a quasi-conical lumen inside the tool, and wherein the guiding surfaces, at the distal end of the lumen, near the exit opening, will have reached a state where a cross section of the lumen is essentially circular.

7. The tool as claimed in claim 1, wherein said guiding surfaces gradually change from the proximal end, where the guiding surfaces do not affect the nominal shape of the wound closure element, towards the distal end where the guiding surfaces force the wound closure element to assume a shape that conforms to an inner lumen of an introducer, connectable to the distal end of said guiding tool.

8. The tool as claimed in claim 1, wherein said lumen is cone shaped at least in the distal region of said guiding tool, and has a large enough diameter in the proximal region of the guiding tool, that the nominal shape of the wound closure element is not affected, and a small enough diameter in the distal end that the wound closure element conforms to an inner lumen of an introducer, connectable to the distal end of said guiding tool.

9. The tool as claimed in claim 1, wherein the proximal region of the tool is essentially cylindrical, forming a storage compartment for said closure element, in which the nominal shape of the wound closure element is not affected.

10. The tool as claimed in claim 1, further comprising guiding rails arranged to prevent the closure element from inadvertent tilting or other incorrect behavior during movement of the closure element through the guiding tool.

11. The tool as claimed in claim 1, further comprising a sealing plug positioned at the introduction opening to minimize leakage of body fluid.

12. The tool as claimed in claim 1, wherein the wound closure element guiding surfaces engage peripheral brim or collar portions of a wound closure element, such that the brim or collar portions are deflected downward from an essentially flat initial position, whereby the wound closure element is capable of passing through said incision or puncture, and whereby after passage through said incision or puncture the wound closure element assumes a shape that is capable of providing a sealing action against said incision or puncture.

13. A system for introduction and securing of a wound closure element into a percutaneous incision or puncture in a wall of a vessel, duct, lumen or hollow organ in a body of a living being, said incision or puncture being smaller than said wound closure element in an unfolded or undeformed state, said system comprising:
- a wound closure element;
- an introducer for introducing said wound closure element into said incision or puncture;
- a pusher device for enabling passage of said wound closure element through said introducer; and
- a guiding tool connectable to said introducer, wherein the guiding tool includes a body having a distal end and a proximal end and a lumen extending between said distal end and said proximal end; a wound closure element introduction opening in the proximal end, and a wound closure element exit opening in the distal end; wherein said lumen has inner walls having wound closure element guiding surfaces adapted to progressively fold a peripheral portion of a wound closure element in a direction toward a non-peripheral portion to reversibly reduce the spatial extension of the wound closure element during passage of the wound closure element through the guiding tool.

14. The system as claimed in claim 13, wherein the wound closure element is made of resorbable material.

15. The system as claimed in claim 11, wherein the wound closure element is stored in an unfolded state.

16. A guiding tool for folding a wound closure element for insertion into an open wound comprising:
- a body having a distal end, a proximal end, and a lumen, wherein the lumen extends between the distal end and the proximal end and includes inner walls;
- an introduction opening in the proximal end;
- an exit opening in the distal end; and
- deformation surfaces positioned on the inner walls, wherein the deformation surfaces are configured to progressively fold a peripheral portion of a wound closure element in a direction toward a non-peripheral portion as the wound closure element moves through the guiding tool.

17. The guiding tool of claim 16, further comprising a sealing plug positioned at the introduction opening to minimize leakage of fluid from the lumen.

18. The guiding tool of claim 16, wherein the exit opening is smaller than the introduction opening.

19. The guiding tool of claim 16, wherein at least one inner wall is flat.

20. The guiding tool of claim 19, wherein the deformation surfaces include deflection elements configured to engage a peripheral portion of the wound closure element so that the peripheral portion is bent downward from an essentially flat position.

21. The guiding tool of claim 16, wherein the lumen includes a cone shaped portion positioned near the exit opening.

22. The guiding tool of claim 16, wherein the lumen is substantially circular near the exit opening.

23. The guiding tool of claim 22, wherein an inner diameter of the lumen near the exit opening corresponds to an inner diameter of an introducer.

24. The guiding tool of claim 22, wherein an inner diameter of the lumen near the exit opening is smaller than a wound opening.

25. The guiding tool of claim 16, further comprising a connection portion at the distal end for connection to an introducer, wherein an exit diameter of the connection portion is equal to or slightly smaller than an inner diameter of the introducer.

26. The guiding tool of claim 16, wherein the deformation surfaces include a first deformation surface and a second deformation surface.

27. The guiding tool of claim 26, further comprising a guiding recess, wherein the guiding recess is positioned between the first and second deformation surfaces.

28. The guiding tool of claim 26, further comprising guiding rails, wherein the guiding rails are positioned above the deformation surfaces.

29. The guiding tool of claim 28, wherein the guiding rails are integral with the lumen.

30. The guiding tool of claim 28, wherein the guiding rails are mechanically attached to the lumen.

31. The guiding tool of claim 26, wherein the first and second deformation surfaces each include a horizontal portion positioned close to the proximal end.

32. The guiding tool of claim 31, wherein the first and second deformation surfaces each include a folding portion positioned between the horizontal portion and the distal end.

33. The guiding tool of claim 32, wherein the folding portion gradually elevates and curves from an essentially horizontal orientation to a state where a cross section of the lumen near the exit opening is essentially circular.

34. The guiding tool of claim 16, further comprising a wound closure element having a peripheral portion and a mid portion, wherein the peripheral portion is substantially thinner and more flexible than the mid portion.

35. The guiding tool of claim 34, further comprising a suture element secured to the wound closure element.

36. The guiding tool of claim 35, further comprising a locking element provided on the suture element.

37. The guiding tool of claim 36, wherein the locking element includes a central hole and wherein the suture element runs through the central hole so that the locking element can be moved along the suture element.

38. The guiding tool of claim 37, wherein the suture element includes a friction element positioned on a distal end of the suture element configured so that when the closure element is brought in contact with an interior wall of a wound, the locking element can be moved along the suture element and pushed against an exterior wall of a wound so that the locking element engages the friction element thereby locking the closure element to seal the wound.

39. The guiding tool of claim 38, wherein the locking element and the friction element are configured to engage in an interference fit to lock the closure element.

40. A system for folding a wound closure element for insertion into an open wound comprising:
- a wound closure element;
- a guiding tool including a body having a distal end, a proximal end, and a lumen, wherein the lumen extends between the distal end and the proximal end and includes inner walls; an introduction opening in the proximal end; an exit opening in the distal end; and deformation surfaces positioned on the inner walls, wherein the deformation surfaces are configured to progressively fold a peripheral portion of the wound closure element in a direction toward a non-peripheral portion as the wound closure element moves through the guiding tool;
- an introducer for introducing the wound closure element into an open wound, wherein the introducer is connected to the guiding tool at the exit opening; and a pusher device configured to move the wound closure element through the introducer.

41. The system of claim 40, further comprising a sealing plug positioned at the introduction opening to minimize leakage of fluid from the lumen.

42. The system of claim 40, wherein the wound closure element is stored in an unfolded state.

43. The system of claim 40, wherein the would closure element is made of a resorbable material.

44. A system for folding a wound closure element for insertion into an open wound comprising:
  a wound closure element;
  a guiding tool including a body having a distal end, a proximal end, and a lumen, wherein the lumen extends between the distal end and the proximal end and includes inner walls; an introduction opening in the proximal end; an exit opening in the distal end; and deformation surfaces positioned on the inner walls, wherein the deformation surfaces are configured to fold the wound closure element as the wound closure element moves through the guiding tool;
  an introducer for introducing the wound closure element into an open wound, wherein the introducer is connected to the guiding tool at the exit opening;
  a pusher device configured to move the wound closure element through the introducer; and
  a suture element secured to the wound closure element and a locking element provided on the suture element.

45. The system of claim 44, wherein the locking element includes a central hole and wherein the suture element runs through the central hole so that the locking element can be moved along the suture element.

46. The system of claim 45, wherein the suture element includes a friction element positioned on a distal end of the suture element configured so that when the closure element is brought in contact with an interior wall of a wound, the locking element can be moved along the suture element and pushed against an exterior wall of a wound so that the locking element engages the friction element thereby locking the closure element to seal the wound.

47. A guiding tool for folding a wound closure element for insertion into an open wound comprising:
  a body having a distal end, a proximal end, and a lumen, wherein the lumen extends between the distal end and the proximal end and includes inner walls;
  an exit opening in the distal end; and
  deformation surfaces positioned on the inner walls, wherein the deformation surfaces are configured to progressively fold a peripheral portion of a wound closure element in a direction toward a non-peripheral portion as the wound closure element moves through the guiding tool.

48. A guiding tool for deforming a wound closure element for insertion into an open wound comprising:
  a body having a distal end, a proximal end, and a lumen, wherein the lumen extends between the distal end and the proximal end and includes inner walls;
  an introduction opening in the proximal end;
  an exit opening in the distal end; and
  guiding surfaces positioned on the inner walls, wherein the guiding surfaces are configured to accept a wound closure element in an undeformed state and to progressively fold the wound closure element during passage of the wound closure element through the guiding tool until a shape of the wound closure element at the exit opening corresponds to the shape of an introducer tube.

49. The guiding tool of claim 48, wherein the guiding surfaces are configured to store the wound closure element in an undeformed state.

50. A guiding tool for deforming a wound closure element for insertion into an open wound comprising:
  a body having a distal end, a proximal end, and a lumen, wherein the lumen extends between the distal end and the proximal end and includes inner walls;
  an introduction opening in the proximal end;
  an exit opening in the distal end; and
  guiding surfaces positioned on the inner walls, wherein the guiding surfaces are configured to accept a wound closure element in an undeformed state and to deform the wound closure element by rolling a peripheral portion of the wound closure element around a longitudinal axis of the wound closure element during passage of the wound closure element through the guiding tool.

51. The guiding tool of claim 50, wherein the guiding surfaces are configured to store the wound closure element in an undeformed state.

52. The guiding tool of claim 50, wherein the guiding surfaces are configured to deform the wound closure element in a gradual manner.

* * * * *